United States Patent [19]

Corn

[11] Patent Number: 5,776,105
[45] Date of Patent: Jul. 7, 1998

[54] AMBULATORY INTRAVENOUS FLUID HOLDER

[75] Inventor: Stephen B. Corn, Sharon, Mass.

[73] Assignee: Children's Medical Center Corp., Boston, Mass.

[21] Appl. No.: 721,804

[22] Filed: Sep. 27, 1996

Related U.S. Application Data

[60] Provisional application No. 60/004,447 Sep. 28, 1995.

[51] Int. Cl.[6] ............................................. A61M 5/32
[52] U.S. Cl. ..................................... 604/174; 604/179
[58] Field of Search ............................... 604/131, 132, 604/153, 174; 128/DIG. 26

[56] References Cited

U.S. PATENT DOCUMENTS

| | | | |
|---|---|---|---|
| 3,468,308 | 9/1969 | Bierman | 128/214 |
| 3,572,340 | 3/1971 | Lloyd et al. | 604/133 |
| 4,090,514 | 5/1978 | Hinck et al. | 128/214 |
| 4,507,116 | 3/1985 | Leibinsohn | 604/142 |
| 4,857,055 | 8/1989 | Wang | 604/133 |
| 4,915,104 | 4/1990 | Marcy | 128/DIG. 26 X |
| 5,074,839 | 12/1991 | Choksi et al. | 604/132 X |
| 5,168,892 | 12/1992 | Sunderland | 137/343 |
| 5,232,439 | 8/1993 | Campbell et al. | 604/28 |
| 5,236,004 | 8/1993 | Sunderland et al. | 137/343 |
| 5,250,027 | 10/1993 | Lewis et al. | 604/65 |
| 5,318,540 | 6/1994 | Athayde et al. | 604/141 |
| 5,336,188 | 8/1994 | Kriesel | 604/132 |
| 5,336,195 | 8/1994 | Daneshvar | 128/DIG. 26 X |
| 5,342,313 | 8/1994 | Campbell et al. | 604/153 |
| 5,348,539 | 9/1994 | Herskowitz | 604/141 |
| 5,356,379 | 10/1994 | Vaillancourt | 604/131 X |
| 5,399,166 | 3/1995 | Laing | 604/131 X |
| 5,482,446 | 1/1996 | Williamson et al. | 604/153 X |
| 5,492,534 | 2/1996 | Athayde et al. | 604/153 X |

*Primary Examiner*—Sam Rimell
*Attorney, Agent, or Firm*—Thomas J. Engellenner; Lahive & Cockfield, LLP

[57] ABSTRACT

Systems and methods for delivery of IV fluid to an ambulatory patient are disclosed. The system includes a holder (e.g., a pouch, strap or web-sling) that secures the a source of infusion fluid to a patient's body. Alternatively, the holder can be in the form of a back pack or a fanny pack. The invention further includes a means for applying pressure to the IV fluid to induce infusion. For example, a pressure gradient can be supplied by an infuser bag or a mechanical pressure infuser that is present within the holder or otherwise coupled to an IV fluid container to exert compressive force thereon. The infuser bag can be inflated (e.g., by hand) and may include a valve to prevent over inflation.

12 Claims, 3 Drawing Sheets

1

AMBULATORY INTRAVENOUS FLUID HOLDER

This application is a continuation of Provisional Application No. 60/004,447 filed Sep. 28, 1995.

BACKGROUND OF THE INVENTION

The technical field of this invention is intravenous delivery of therapeutic fluids and, in particular intravenous delivery systems that are especially adapted to ambulatory patients. The systems of the invention provide added safety and convenience for the patient.

Ambulation for the in-hospital patient is a common occurrence. In fact, early ambulation of the post-surgical patent has been shown to decrease respiratory morbidity in the post operative period. However, the patients in most need of early ambulation are usually those that have intravenous (IV) infusions in place. Ambulation for such patients can be difficult since they are usually required to push a wheeled IV pole having a large IV fluid bag attached. The IV pole usually is quite tall in order to establish a sufficient pressure gradient while the patient is in the upright position. Also, the pole must have a wide base to increase its stability.

The height of the pole and the breadth of the base can lead to difficult and dangerous ambulation conditions for the patient. Numerous incidents have been reported of patient and/or visitor injuries resulting from such ambulatory IV poles. Aside from the dangers associated with the use of such IV poles for ambulatory patients, these poles also lack convenience. For example, it is difficult to carry items, such as cafeteria trays, while pushing such an IV pole. Accordingly, there is a need for improved intravenous delivery systems that are specially adapted for ambulatory patients. Such improved systems would ideally provide added safety and convenience for the patient.

SUMMARY OF THE INVENTION

Systems and methods for delivery of IV fluid to an ambulatory patient are disclosed. The system includes a holder (e.g., a pouch, strap or web-sling) that secures the a source of infusion fluid to a patient's body. Alternatively, the holder can be in the form of a backpack or a fanny pack. The invention further includes a means for applying pressure to the IV fluid to induce infusion. For example, a pressure gradient can be supplied by an infuser bag or a mechanical pressure infuser that is present within the holder or otherwise coupled to an IV fluid container to exert compressive force thereon. The infuser bag can be inflated (e.g., by hand) and may include a valve to prevent over inflation.

In one illustrated embodiment, a conventional IV bag is placed in contact with a pressurizable infuser bag, both of which can be held within a flexible holder. A drip chamber is vertically oriented and held in place outside (or inside) of the flexible holder.

An IV line extends from the drip chamber to a desired location on the patient's body to infuse the intravenous fluid into the patient. A roller clamp can also be incorporated into the IV line.

The invention will next be described in connection with certain illustrated embodiments. However, to be clear that various changes and modifications can be made by those skilled in the art without departing from the spirit or scope of the invention.

BRIEF DESCRIPTION OF THE DRAWINGS

The invention may be more fully understood from the following description when read together with the accompanying drawings in which.

DETAILED DESCRIPTION

Figure 1:
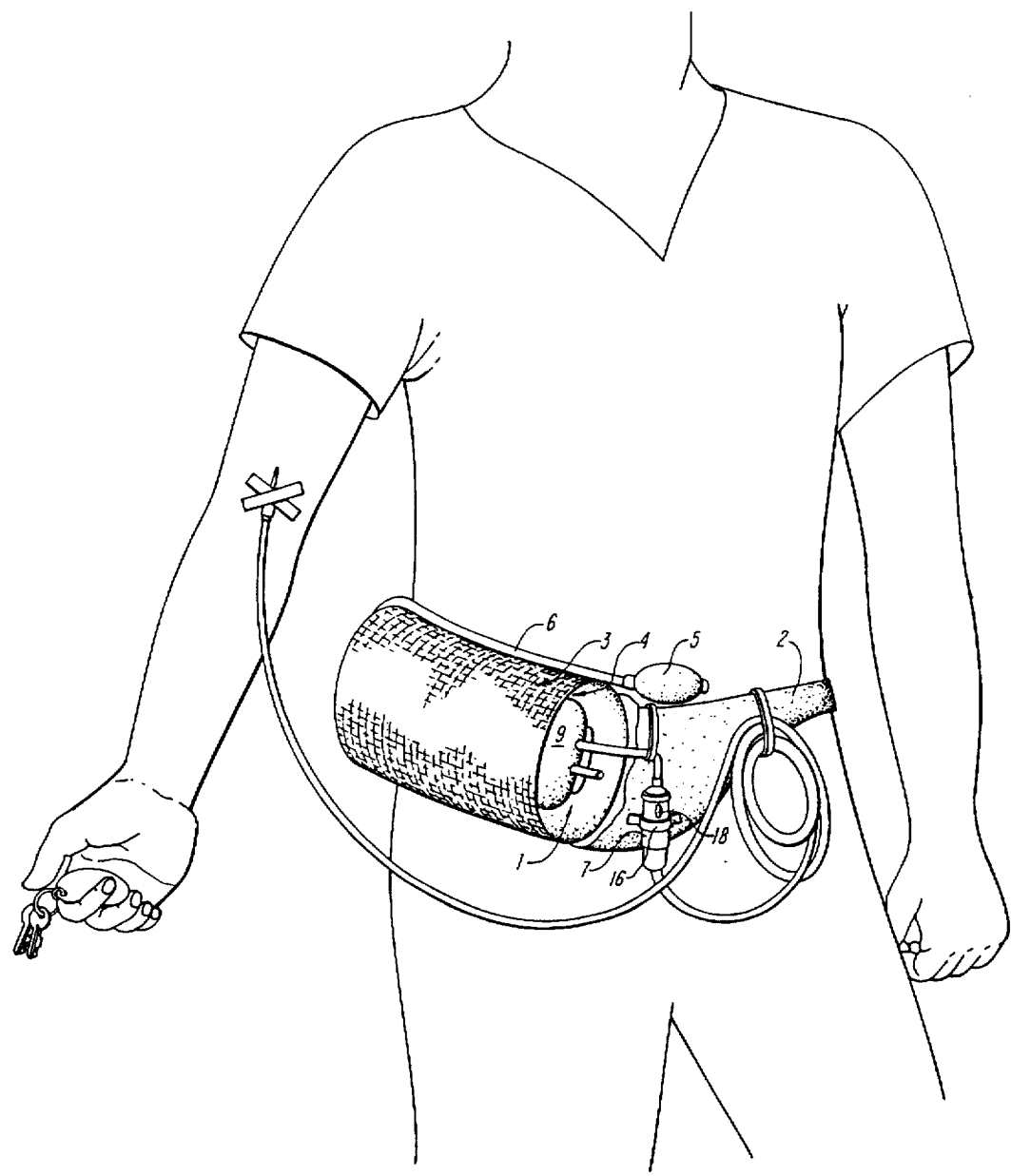
FIG. 1 is a schematic, perspective view of an ambulatory intravenous fluid holder according to the invention.

In FIG. 1 an apparatus according to the invention is shown including an infuser bag 1 is affixed to a strap 2, which can be secured to the patient. In the illustrated embodiment, the infuser bag has appended thereto an inelastic fabric layer 3 so as to form a pouch or space 4 between the fabric layer and the infuser bag 1. In use, an IV bag 9 can be placed within pouch 4. The pouch 4 preferably is open at least one end (or both ends as shown) to accommodate the egress of IV tubing. In an alternative embodiment, the fabric pouch can be replaced by a more elaborate structure in the form of a belly, back or fanny pack which includes an accessible inner chamber. The infuser bag 1, which is configured to exert a compressive force on an IV bag 9, is disposed within the pouch (or within a chamber of a pack). A common IV line leads out of the IV bag, and out of the pouch/chamber, to a drip chamber 7 that is disposed outside of the pack. The drip chamber 7 can be connected to the holder via a mounting element 16 which is preferably includes a swivel or gimbel mount to ensure that the drip chamber is maintained in a substantially vertical position. The drip chamber can further include a sensor 18 with a visible or audible alarm in the event that the drip chamber deviates from vertical or is otherwise compromised. A separate IV line extends from an outlet port on the drip chamber to a catheter that enters the patient's body.

Figure 2:
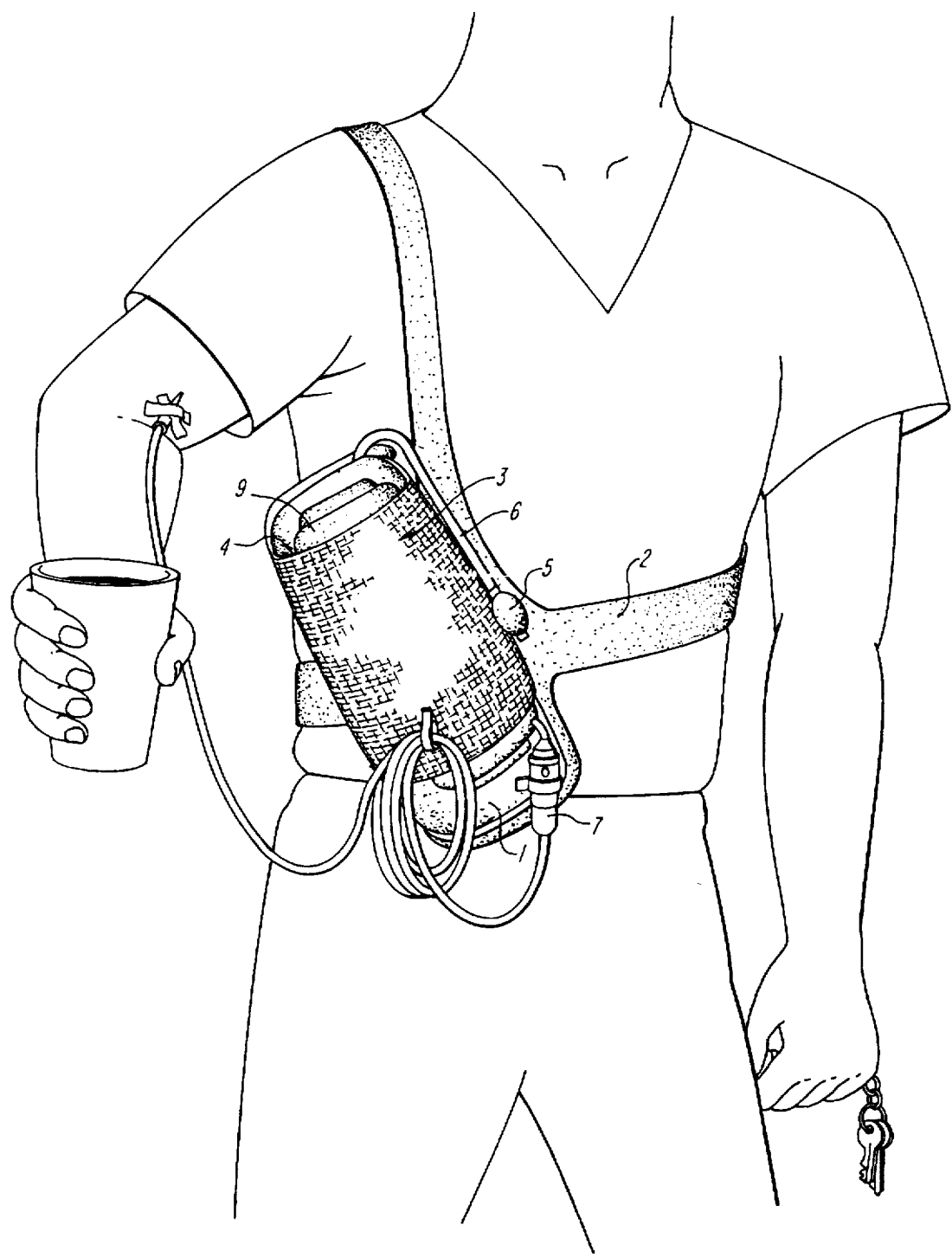
FIG. 2 is a schematic, perspective view of another embodiment of an ambulatory intravenous fluid holder according to the invention.

In FIG. 2 a similar structure is shown in conjunction with a shoulder belt rather than a simple waist belt. In certain applications, the embodiment of FIG. 2 may be preferred for comfort, ease of use and/or orientation purposes.

Figure 3:
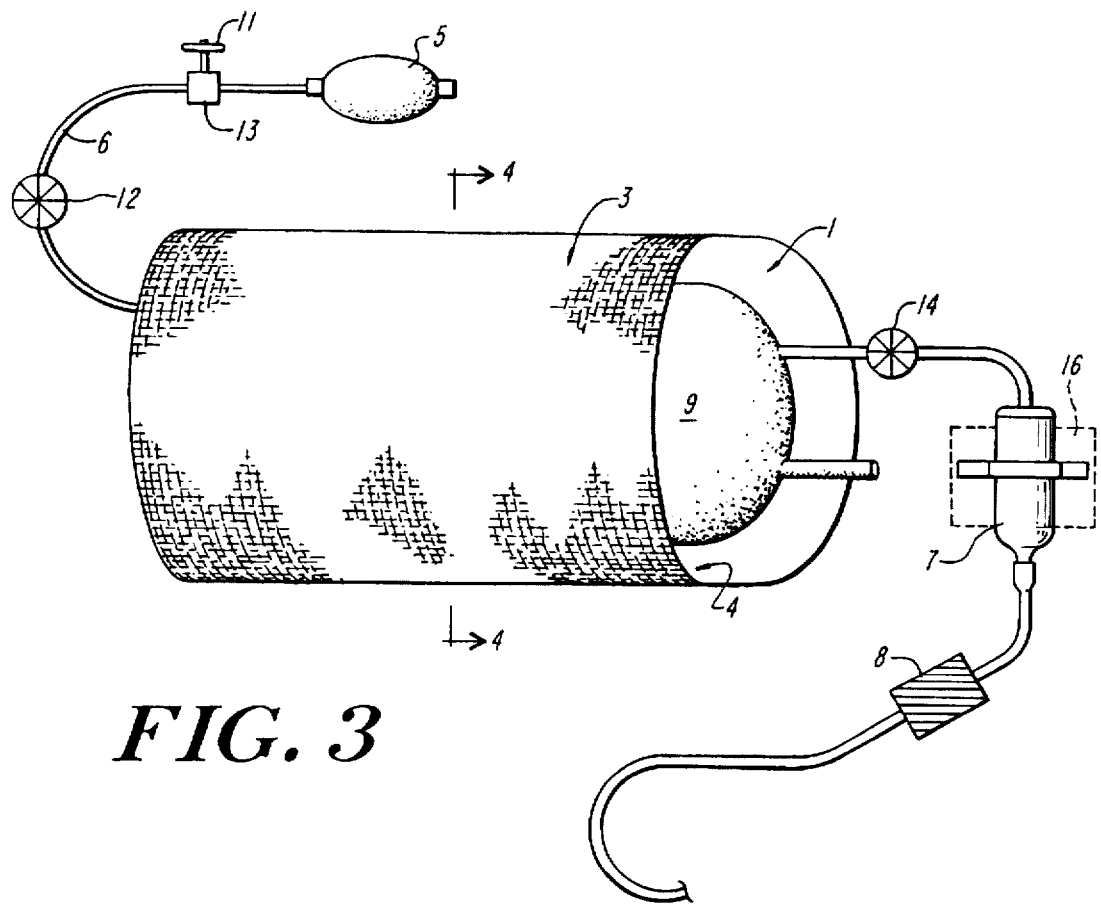
FIG. 3 is a more detailed schematic view of a holder and pressurization means according to the invention.

With reference to the more detailed illustration of FIG. 3, as well as FIGS. 1 and 2, the means for applying pressure to the IV fluid can include an infuser bag 9 with an inflatable (pressurizable) bladder. The bladder can be pressurized by air pressure through a mechanical pump. In one embodiment a compressible bulb 5 is used to pressurize the bladder. The bulb communicates air pressure through a conduit 6 to the bladder. Preferably, a 3-way valve mechanism 11 controls the flow of air pressure into the bladder and allows pressure to be directed to the bladder, maintained in the bladder, or released from the bladder. The infusion bag can also include a pressure gauge 12 to indicate the level of pressure within the bladder. The infusion bag assembly can further include a pressure release valve 13 which is able to bleed off pressure within the bag in the event of over pressurization. Various infuser bag designs are known in the art. One exemplary, commercially available, infuser bag is the INFUSABLE ® disposable pressure infuser available from Vital Signs, Inc., of Totowa, N.J.

A conventional IV bag can be used as the infusion source to hold the intravenous fluid. Such IV bags are well known in the art and are made of a clear, flexible plastic material. A suitable IV bag also includes at least one outlet port to which IV tubing or other suitable conduits may be attached.

Figure 4:
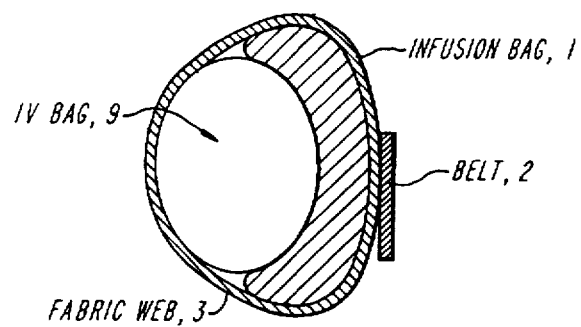
FIG. 4 is a cross-sectional view of the apparatus of FIG. 3 along line 4—4.

FIG. 4 is a cross-sectional view of the holder assembly of FIG. 3 further illustrating the apparatus of the present invention including belt 2, infusion bag 1, fabric web 3 and IV fluid container 9.

One of ordinary skill in the art will appreciate that standard infusion tubing can be used for this invention. In the illustrated embodiments, a length of IV tubing extends from an outflow port on the IV bag to a drip chamber 7. Preferably, the drip chamber 7 is disposed in a visible position outside of the pouch/pack and is maintained in a vertical position. In one embodiment the drip chamber can be secured via a drip chamber mounting element 16 to the belt or strap 2 that affixes the system to the patient. The mounting element 16 can also include a swivel joint or a self-righting mechanism to maintain the drip chamber in a substantially vertical orientation.

In a preferred embodiment, with the drip chamber vertically positioned, an outflow conduit extends from the IV bag and conveys fluid to a top portion of the drip chamber. A separate length of IV tubing connects to another port at the bottom section of the drip chamber and communicates fluid to a catheter which can be inserted within a patient.

The IV tubing can further include a roller clamp 8 or similar device attached thereto and disposed downstream of the drip chamber to regulate the fluid flow rate. Also, the infusion tubing may include a pressure gauge 14, various valves (such as two- or three-way valves) to regulate fluid flow and to allow infusion flow of different medicaments. Syringe ports may also be present within the infusion tubing.

The system of this invention can also include attachment sites for IV accessories, remote beepers, remote patient tracking devices, and monitors. Attachment sites for such devices may be placed on the straps, the infuser bag, or the flexible pack.

In a preferred method of treatment according to the invention, the ambulatory IV system of the invention can be operated as follows. The infusion bag is attached to a strap element that secures the system to a patient's body. An inelastic fabric layer, such as a web or mesh fabric, is attached to one of the surfaces of the infusion bag such that a space is formed between the infusion bag and the fabric. In one embodiment, fabric attaches only to the infusion bag at side portions thereof, leaving openings at either end of the assembly to accommodate the egress of tubing. The IV bag is placed within the space formed between the infusion bag and the web. Once the infusion bag is properly positioned, the infusion bag is pressurized, e.g., using a hand pump. Pressurization of the fluid bag communicates a compressive force to the IV bag. This compressive force causes fluid within the IV bag to be forced out of the bag and into the drip chamber. So long as the drip chamber is maintained in a substantially vertical orientation, a controlled flow of IV fluid will be delivered via the IV tubing to the patient.

Among the advantages of the system of this invention is that it offers a simple and easy-to-use means for allowing an IV dependent patient to ambulate in a hospital, or at home, without creating a hazardous situation for the patient or for other individuals as a result of the use of a wheeled IV pole. The device benefits all IV-dependent patients who ambulate within a hospital or other environments. This includes ward patients, post surgical patients and ambulatory day-surgery patients who are usually required to ambulate and void before discontinuation of IV therapy. Additionally, many patients receive home antibiotic therapy. Most homes are not designed to accommodate a mobile IV pole due to door saddles, stairs, carpeting, and uneven flooring. The device of the present invention allows any home IV patient to ambulate safely and effectively.

I claim:

1. An ambulatory intravenous fluid delivery system comprising:

a holder for securing a source of intravenous fluid to a patient's body;

pressurization means for applying pressure to the intravenous fluid to induce infusion;

an infusion line adopted to delivery fluid from the source to a patient;

a drip chamber disposed between the source of intravenous fluid and the infusion line through which the fluid can flow in a controlled manner; and a drip chamber mounting element for mounting the drip chamber to the holder, the mounting element serving to maintain the drip chamber in a substantially vertical orientation in use.

2. The system of claim 1 wherein the holder further comprises at least one belt for encircling a patient's body.

3. The system of claim 1 wherein the holder further comprises at least one shoulder strap.

4. The system of claim 1 wherein the holder further comprises at least one pouch-forming element for holding an intravenous fluid source.

5. The system of claim 1 wherein the pressurization means further comprises a mechanical pressure infuser.

6. The system of claim 1 wherein the pressurization means further comprises an pressurizable infuser bag having an inflatable chamber.

7. The system of claim 6 wherein the pressurization means further comprises a manual pump for inflating the infuser bag.

8. The system of claim 6 wherein the pressurization means further comprises a valve to prevent over inflation of the infuser bag.

9. The system of claim 6 wherein the pressurization means further comprises a pressure gauge for measuring the pressure within the infuser bag.

10. The system of claim 1 wherein the system further comprises a conduit for conveying intravenous fluid between the infusion source and a drip chamber.

11. A method of delivering intravenous fluid to an ambulatory patient comprising:

securing a source of intravenous fluid to a patient's body via a holder;

connecting an infusion line having a vertically-oriented drip chamber and a stop valve to the source;

mounting the drip chamber to the holder via a mounting element that ensures that the drip chamber is maintained in a vertically orientation so that fluid can flow through the drip chamber from the source of intravenous fluid to the infusion line in a controlled manner;

applying pressure to said source; and opening said stop valve so that the fluid can be delivered to the patient.

12. A system of claim 1 wherein the mounting element further comprises a swivel mechanism to maintain the vertical orientation of the drip chamber.

* * * * *